United States Patent [19]

Sostegni

[11] Patent Number: 4,813,961
[45] Date of Patent: Mar. 21, 1989

[54] DAMPENER FOR A BEARING ARTHRO-PROTHESIS

[75] Inventor: Giuliano Sostegni, Sesto Fiorentino, Italy

[73] Assignee: Chenil Cont. S.p.A., Italy

[21] Appl. No.: 62,457

[22] Filed: Jun. 12, 1987

[30] Foreign Application Priority Data

Jul. 9, 1986 [EP] European Pat. Off. ........ 86830197.9

[51] Int. Cl.⁴ ............................ A61F 2/32; A61F 2/30
[52] U.S. Cl. ............................................ 623/22; 623/18
[58] Field of Search .................... 623/22, 23, 16, 18, 623/19, 20

[56] References Cited

U.S. PATENT DOCUMENTS

| | | | |
|---|---|---|---|
| 3,818,512 | 6/1974 | Shersher | 623/22 |
| 3,916,451 | 11/1975 | Buechel et al. | 623/22 X |
| 3,938,198 | 2/1976 | Kahn et al. | 623/22 |
| 4,262,369 | 4/1981 | Roux | 623/22 X |
| 4,314,381 | 2/1982 | Koeneman | 623/22 |

FOREIGN PATENT DOCUMENTS 0066092 12/1982 European Pat. Off. ............ 623/22
WO86/02261 4/1986 PCT Int'l Appl. .................. 623/22

Primary Examiner—Ronald L. Frinks
Attorney, Agent, or Firm—McGlew and Tuttle

[57] ABSTRACT

Dampener for a bearing arthro-prosthesis made up of a cradle (1) with a base zone of spherical shape to be interposed between the presser, head (3,2) and the cotyle (4) of the prosthesis, which has stepped cross-section, in the meridian plane, with a thin wall (10), a first central step (11) rising from the bottom of the cradle and more circumferential spaced apart steps (12) being parallel to and coaxial with the central step (11) and having lesser height than the first step. In this way, it is possible to obtain, with a non-compressible material, a variable rigidity of the cradle when subjected to loads applied to the prosthesis as well as maximum deformation increment at the lowest values of the load (approx. 100 kg).

8 Claims, 3 Drawing Sheets

DAMPENER FOR A BEARING ARTHRO-PROTHESIS

BACKGROUND OF THE INVENTION

Field of the Invention

The present invention relates to a dampening element for a bearing arthro-prosthesis.

It is known in the field that during the simplest dynamic phase like a slow pace, the stress that a bearing prosthesis has to sustain, especially the hip, reaches and goes beyond a load of at least five times the patient's weight. Under such conditions, at least two major problems arise with the implants of hip prostheses, that is, first, the steadiness of the implant at the prosthesis-bone interface and, secondly, the load dampening effect in the articulation of the limb. Given the state of the art, the implant steadiness may now be considered as positively achieved, both in the direct implant prostheses and in those having cement-mediate implant. However, the dampening of the load in the articulation has made so little progress that the stresses delivered from the head to the cotyle of the prostheses result of increasing and almost peak-growing intensity during one foot bearing, and so with hardly or no deformation of the joint.

The early attempts made to solve this problem consist of the interposition of a pad of biocompatible plastic material between the femoral head and the cotyle of a hip prosthesis, fully enveloping the prosthesis head thus making both the concave and convex surfaces of the pad smooth and of a constant thickness at any point of the pad. The results that have been achieved to date are completely negative owing to the very high and constant rigidity of the pad even under low loads due, in turn, to the non-compressibility of the material used. More recently, sheaths made of the same plastic material have been adopted partially enclosing the prosthesis head and providing the convex surface with through holes or, channels distributed according to the sheath meridians and parallels, communicating to each other with the intent being to decrease their capacity upon the crushing of the sheath under load. Also these known types of sheaths exhibit a very limited deformation in the load direction such that they do not perform the function of dampening the shocks to which the joint is subjected during the deambulation and more so, especially during low loads. The simulation tests that have been carried out have highlighted this circumstances which is confirmed by the fact that, after some time, the sheath exhibits a concavity due to wear in the zone of maximum stress.

SUMMARY OF THE INVENTION

The present invention has, as its object, significantly improving the elasticity of the joint of the bearing prostheses by allowing the stresses due to deambulation to be dampened more effectively, particularly the stresses of low value.

This result has been achieved according to the invention by adopting the idea of realizing a cradle made of biocompatible, non-compressible plastics to be interposed between the femoral head and the cotyle of a bearing prosthesis. The rigidity of this cradle increases gradually under sudden loads transmitted by the articulation. Further, the cradle includes an internal surface with a first cylindrical step rising from the bottom zone of the cradle and the cradle is of such a height as to result always in contact with the corresponding zone of the prosthesis head. The cradle has additional continuous circumferential steps being spaced apart and parallel to and coaxial with the first step, and whose height is less than that of the first step, in order to allow the steps to come in contact—under growing loads—with corresponding zones of the prosthesis head, in succession, from the bottom towards the cradle base.

The advantages obtained through the present invention lie essentially in the fact that a dampener for arthro-prostheses, according to the invention, has a low rigidity at low compression loads (ratio between the applied force (or stress) and attained deformation (or strain). Another advantage of the prostheses is that the rigidity of the cradle increases progressively, slowly at first and the more rapidly, with the increasing stress.

A further advantage of the embodiment is that it is possible to change the cotyle position in order to orient the cradle axis according to the direction of the articulation maximum stress. Additional advantages of the embodiment are that it is possible to adjust the axial amplitude of the deformation and the prosthesized joint exhibits a friction torque lower than the sheaths for arthro-prostheses presently used. A further object of the invention is that it has a simple design and is easy to realize in different sizes to fit the anatomical needs of various patients while also being rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

DESCRIPTION OF THE PREFERRED EMBODIMENT

Figure 1:
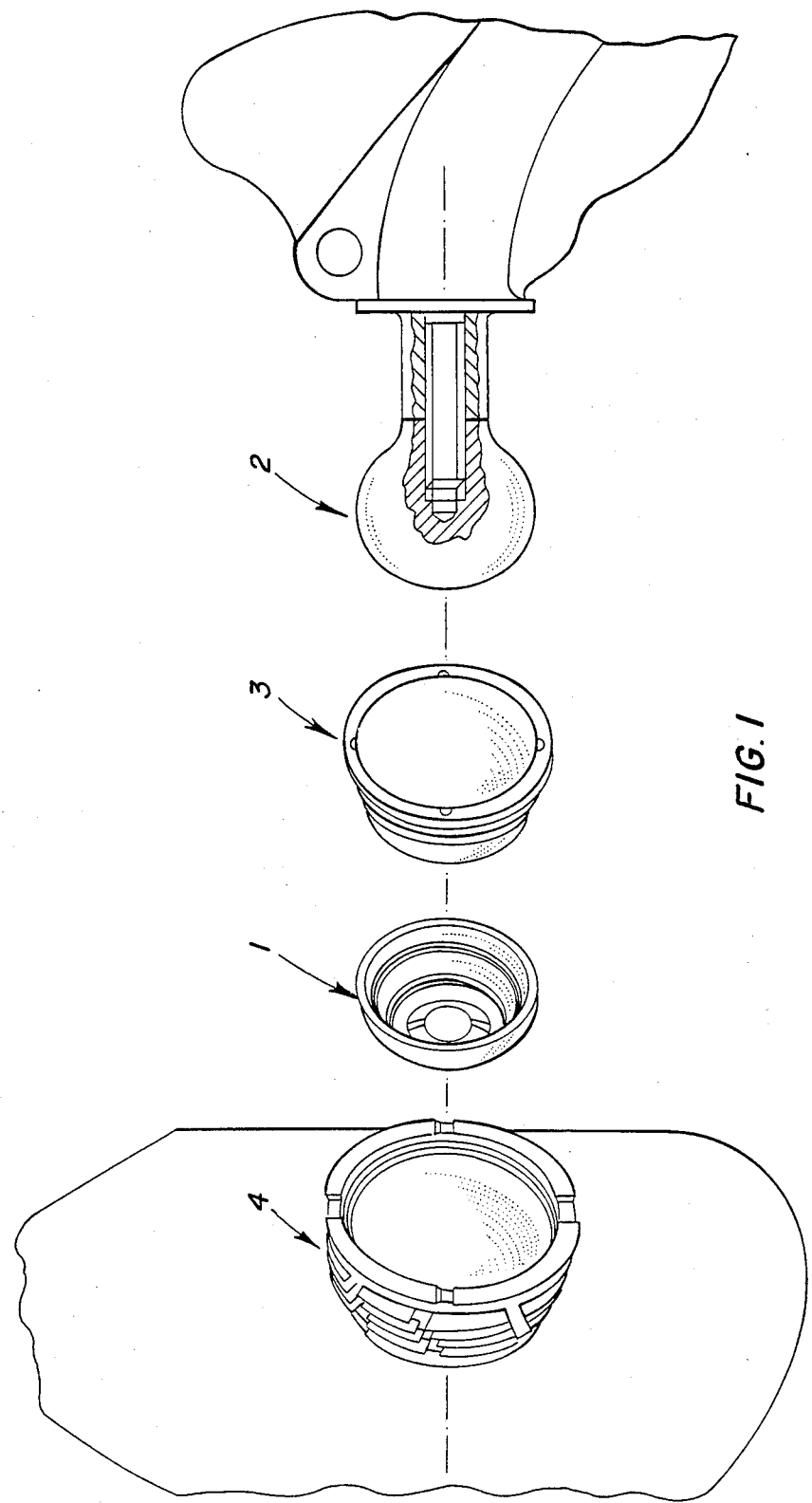
FIG. 1 shows a perspective exploded view of a hip prosthesis complete with a dampening element according to the invention.
Figure 2:
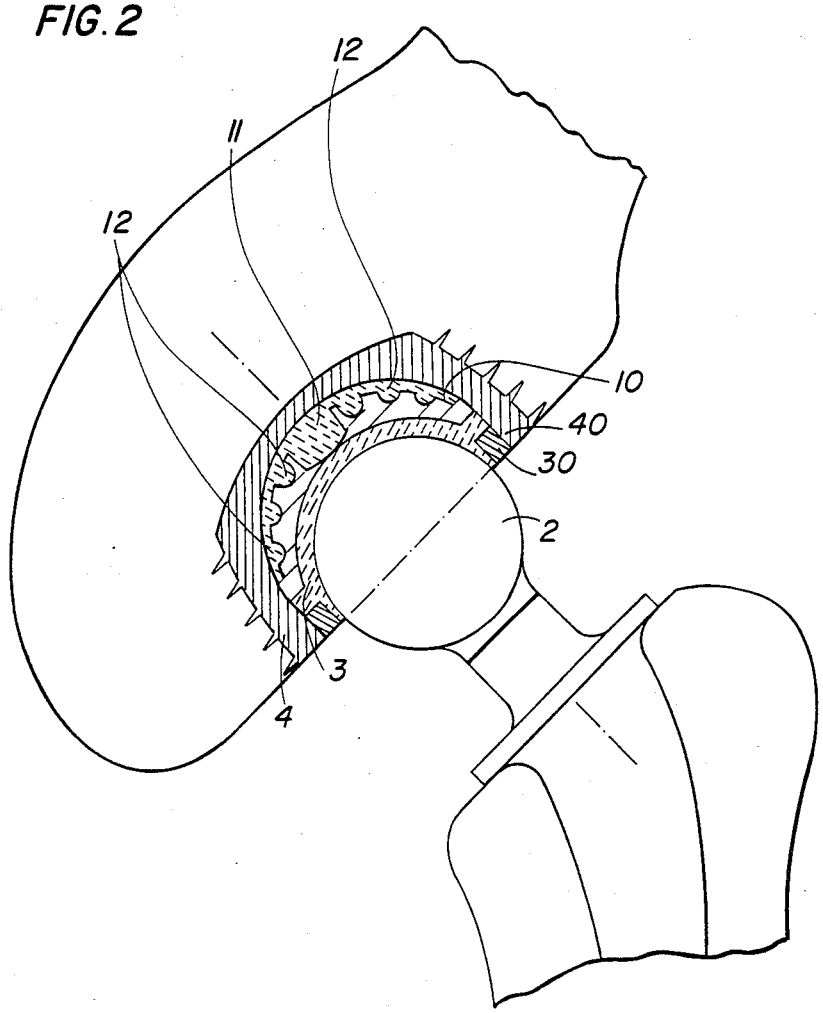
FIG. 2 shows the diametrical section of the prosthesis of FIG. 1 as it appears when implanted.

FIGS. 1 and 2 show a complete cradle 1 for a hip prosthesis which comprises a metal femoral head 2, a polyethylene presser 3 to be fitted on the head 2, and a metal cotyle 4 to be fixed to the acetabulum of the patient. The cradle 1 consists of a body with a unibase spherical zone shape whose height is slightly less than the outer radius of the presser 3, and with the outer surface of the cradle 3 being smooth such that it is intended to engage into the corresponding cotyle cavity 4. The cross-section of the cradle 1 taken along a plane passing through a meridian is stepped-like, that is, with a thin wall 10, a first central step 11 rising from the thin wall 10 in correspondence with the bottom of the cradle 1. The central step 11 is shaped like a circular cylinder and with three circumferential, spaced apart, steps 12 being parallel and coaxial to the central step 11.

The circumferential steps 12 have equal radial development and are spaced apart at a distance greater than their width. The central step 11 has a height much greater than that of the other steps 12 and step 11 has a bearing surface which is approximately ⅛ to 1/16 of the active surface of the presser 3. In this way, with the prosthesis at rest, only the step 11 is in contact with the coresponding zone of the presser 3 (see FIG. 2). With the prosthesis under stress, but for low values thereof, only the central step 11 is affected by the compression and, by undergoing large strain increments, it allows a high dampening of the load on the articulation. For greater values of stress, the presser 3 comes successively in contact with the circumferential steps 12 beginning with the one which is closest to the bottom of the cradle and ending with the farthermost one, thereby bringing about an increase of the cradle rigidity with correspondingly small strain increments.

A screw ring nut 30 which, by engaging a corresponding threaded section 40 of the cotyle 4, keeps retaining the presser 3 advantageously allowing the distance of the presser 3 from cradle 1 to be changed in advance and thus simultaneously effecting a fine adjustment of the cradle rigidity in respect to the patient's weight. It should be apparent that the cradle 1 is coaxially housed within the cotyle 4, and that the cotyle 4 is to be implanted inside the acetabulum and properly inclined thereto, such that the patient's weight will coincide with the direction of maximum stress on the prosthesis.

According to the invention, the central step 11 and the circumferential steps 12 are developed on the cradle convex surface instead of on the concave one. Another possible embodiment (not shown) is to have the central step 11 and the circumferential steps 12 evenly developed on both the concave and convex sides of the cradle.

For example, the following are geometrical values of the basic components of a hip prosthesis provided with a dampener according to the invention and are indicated hereinafter relative to a form considered as characteristic for its installation.

Figure 3:
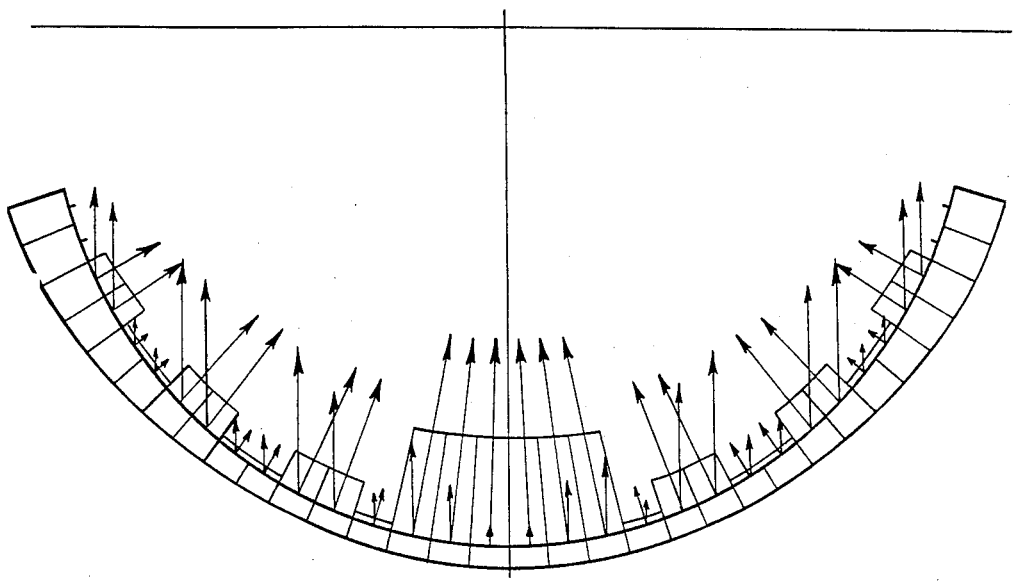
FIG. 3 shows the reactions distribution along a concentric arc for a hip prosthesis according to the invention in a practical embodiment.

Presser: R=19 mm
Cradle: R=22 mm
Max deformation=4 mm
Height of central step H=5 mm
Diameter of central step $\phi$=10 mm
Number of circumferential steps: 3 cross-section
Height of circumferential steps H=2 mm FIGS. 3 of the attached drawings shows the distribution of the radial forces and of those parallel to the direction of compression deformation of said cradle 1 during the simulated exercise with physiological loads (approximately 100 kg).

Figure 4:
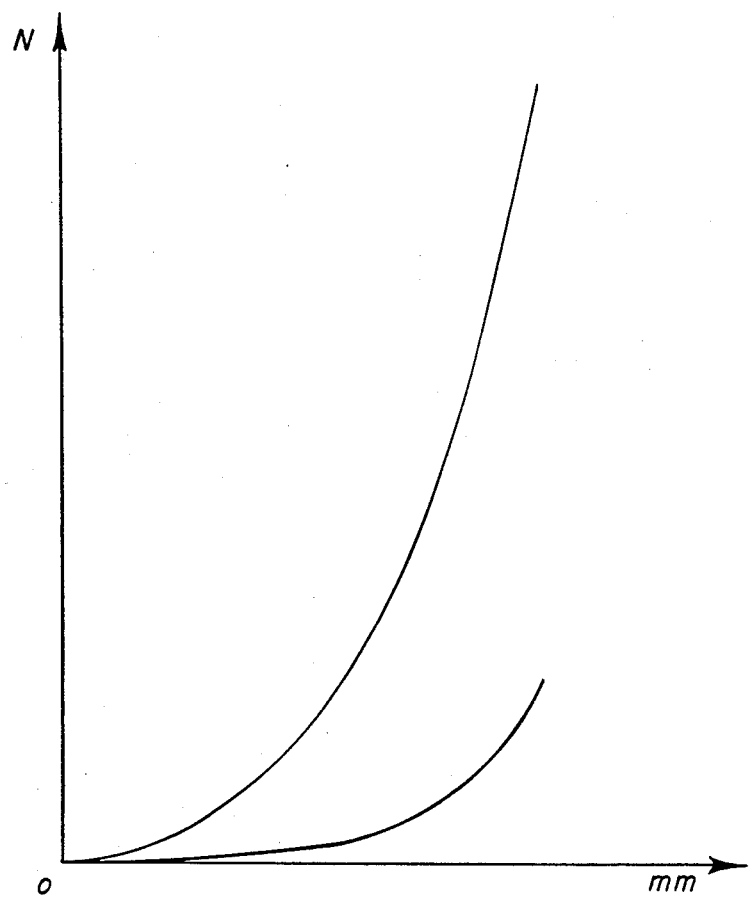
FIG. 4 shows the stress/strain curve (N/mm) (force/deformation) of the cradle for hip prosthesis of FIG. 3 as compared with a traditional sheath.

The lower curve of the diagram of FIG. 4 shows the deformation variation of the central step 11 of the cradle 1 under simulated physological loads to be up to 4 mm. The upper curve of the same diagram shows the same deformation variations of an equally dimensioned traditional sheath for a hip prosthesis under the same simulated physiological loads. A comparison of the two curves in FIG. 4 discloses the fact that with the dampening cradle for bearing prostheses practiced according to the invention, during most physiological loads of the articulation, significant increments of deformation take place at low loads (approximately 100 kg) and, according to the invention, small increments of deformation occur at higher loads (beyond kg). This is a confirmation of the fact that the cradle 1, before transmitting elevated stresses, becomes significantly strained in its least resistant part, the central step 11. Simulated tests have shown that, when the stress on the articulation stops, the cradle 1 reacts equally with an unsteady modulus of elasticity, contrary to the traditional sheath behavior. The cradle experiences a greater deformation for a given force during the reduction of stress than the deformation experienced during the increase of the same given force. Thus, according to the function $\epsilon\chi=0.35-3.45\ L/\Delta$ the corresponding N/mm discharge curve results in being shifted to the right in respect to the charge curve (see FIG. 4). The area subtended between the two curves represents the modest dissipation of energy due to the hysteresis dampening effect which does not cause the problem of excessive heating build-up in the cradle.

While specific embodiments of the invention have been shown and described in detail to illustrate the application of the principles of the invention, it will be understood that the invention may be embodied otherwise without departing from such principles.

I claim:

1. A prosthesis device adapted for connection between a first and second bone comprising:
   a prosthesis cotyle adapted to be affixed to a first bone;
   a hemispherical cradle including a thin wall portion, a first central step portion, and at least one ring step member coaxial with said central step member protruding away from said wall member and away from said cotyle;
   a hemispherical presser head postioned adjacent and coaxial with said cradle so as to be housed within said cradle; and,
   a head adapted to be fixed to a second bone, said head adapted to be inserted in said presser.

2. A dampener for a bearing arthro-prosthesis, comprising:
   a cradle, having a uni-base spherical zone shape, said cradle capable of engaging, on the one side, a corresponding prosthesis presser and prosthesis head; and on the other side, of being housed in a cavity of a corresponding prosthesis cotyle, said cradle having a stepped cross-section in the vertical plane, and including a first central cylindrical step rising from a central zone of the concave-convex surface wall of said cradle, a thin wall, at least one second circumferential step rising from the same side of the first said step relative to the placement of the said step in respect to the thin wall of said cradle, said second step being spaced coaxial and parallel to said first step.

3. A dampener for a bearing arthro-prosthesis according to claim 2, wherein said cradle is characterized as having a height less than that of the said corresponding prosthesis presser and prosthesis head, with which said cradle is engaged.

4. A dampener for a bearing arthro-prosthesis according to claim 2, wherein said central step of said cradle is characterized by having a height greater than that of said circumferential steps and having an active base with a surface ranging from ⅛ to 1/16 of the active surface of said corresponding prosthesis presser and said corresponding prosthesis head with which said cradle is engaged.

5. A dampener for a bearing arthro-prosthesis according to claim 2, wherein said steps of said cradle are equal in height to the radial direction.

6. A dampener for a bearing arthro-prosthesis according to claim 2, wherein each said circumferential step has a semicircular cross-section.

7. A dampener for a bearing arthro-prosthesis according to claim 2, wherein each said circumferential step is at a mutual distance greater than its own height.

8. A dampener for a bearing arthro-prosthesis according to claim 2, wherein the tolerance for the coupling of said cradle with said prosthesis presser is adjusted by means of a screw ring nut.

* * * * *